(12) United States Patent
Grant et al.

(10) Patent No.: US 6,656,193 B2
(45) Date of Patent: Dec. 2, 2003

(54) DEVICE FOR ATTACHMENT OF BUTTRESS MATERIAL TO A SURGICAL FASTENING DEVICE

(75) Inventors: Richard L. Grant, Cincinnati, OH (US); Mark S. Zeiner, Batavia, OH (US); Geoff Hueil, Mason, OH (US); Kenneth Wales, Mason, OH (US); Dean L. Garner, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 55 days.

(21) Appl. No.: 09/850,374

(22) Filed: May 7, 2001

(65) Prior Publication Data

US 2002/0165563 A1 Nov. 7, 2002

(51) Int. Cl.7 .............................................. A61B 17/04
(52) U.S. Cl. ....................... 606/151; 606/139; 606/219; 606/220; 227/175.1; 227/175.2; 227/176.1; 227/179.1
(58) Field of Search ................................ 606/151, 139, 606/219, 220; 227/175.1, 175.2, 176.1, 179, 179.1; 623/1.42

(56) References Cited

U.S. PATENT DOCUMENTS

| | | | |
|---|---|---|---|
| 4,605,730 A | | 8/1986 | Shalaby et al. |
| 4,863,088 A | * | 9/1989 | Redmond et al. .............. 227/19 |
| 5,133,739 A | | 7/1992 | Bezwada et al. |
| 5,263,629 A | * | 11/1993 | Trumbull et al. ............ 128/898 |
| 5,364,001 A | * | 11/1994 | Bryan ...................... 227/175.1 |
| 5,395,034 A | * | 3/1995 | Allen et al. ............... 227/178.1 |
| 5,397,324 A | * | 3/1995 | Carroll et al. ............... 128/898 |
| 5,415,334 A | | 5/1995 | Williamson, IV et al. |
| 5,441,193 A | * | 8/1995 | Gravener .................. 227/175.1 |
| 5,468,253 A | | 11/1995 | Bezwada et al. |
| 5,503,638 A | | 4/1996 | Cooper et al. |
| 5,507,426 A | * | 4/1996 | Young et al. ............. 227/176.1 |
| 5,597,107 A | | 1/1997 | Knodel et al. |
| 5,702,409 A | | 12/1997 | Rayburn et al. |
| 5,752,965 A | | 5/1998 | Francis et al. |
| 5,766,188 A | * | 6/1998 | Igaki ........................... 606/139 |
| 5,810,855 A | | 9/1998 | Rayburn et al. |
| 5,895,412 A | | 4/1999 | Tucker |
| 5,902,312 A | | 5/1999 | Frater et al. |
| 5,964,774 A | | 10/1999 | McKean et al. |
| 6,010,054 A | * | 1/2000 | Johnson et al. .......... 227/176.1 |
| 6,045,560 A | * | 4/2000 | McKean et al. ......... 227/180.1 |
| 6,109,500 A | * | 8/2000 | Alli et al. ................. 227/175.2 |
| 6,325,810 B1 | * | 12/2001 | Hamilton et al. ........ 227/175.1 |

FOREIGN PATENT DOCUMENTS

| | | |
|---|---|---|
| DE | 199 24 311 A | 11/2000 |
| EP | 1064883 A1 | 1/2001 |
| WO | WO 98 38923 A | 11/1998 |

* cited by examiner

Primary Examiner—Gregory L. Huson
Assistant Examiner—Azy Kokabi
(74) Attorney, Agent, or Firm—Dean Garner

(57) ABSTRACT

An assembly for releasably attaching a buttress material onto a tissue clamping member of a surgical stapling device is disclosed. The assembly has a substantially rigid frame for connecting to a top surface of a tissue clamping member of a surgical stapling device when the assembly is disposed thereon. A buttress material is attached to first and second sides of the frame for abutting against a bottom surface of a tissue clamping member of a surgical stapling device when the assembly is disposed thereon.

15 Claims, 10 Drawing Sheets

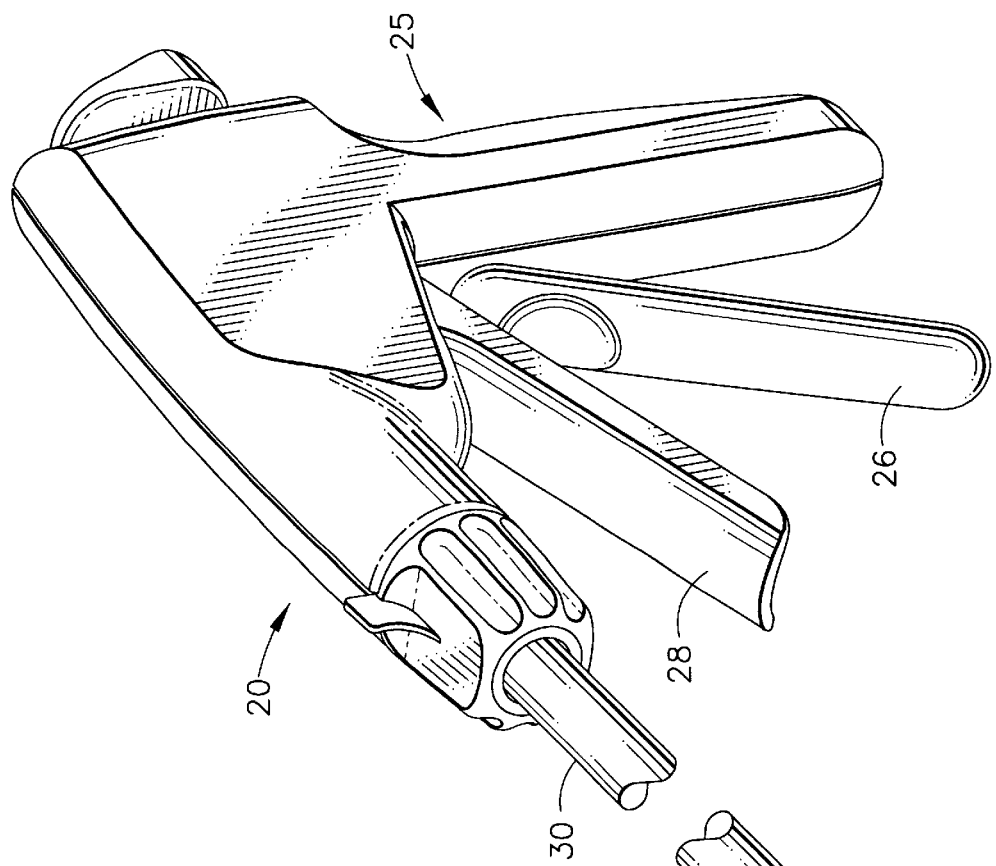
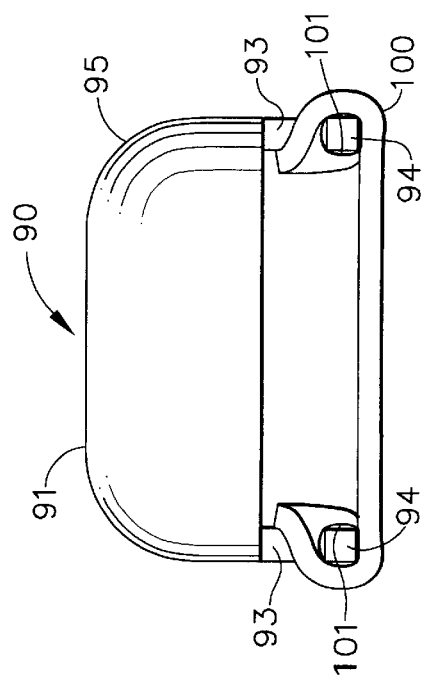
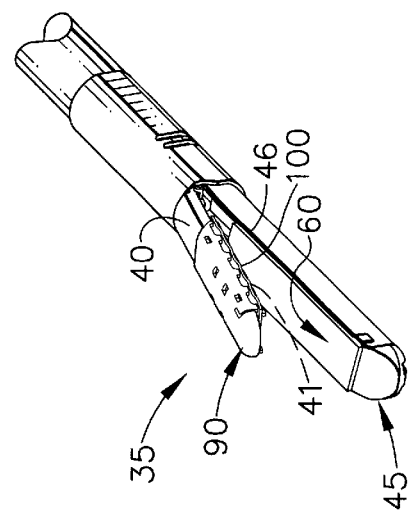
FIG. 6
FIG. 9

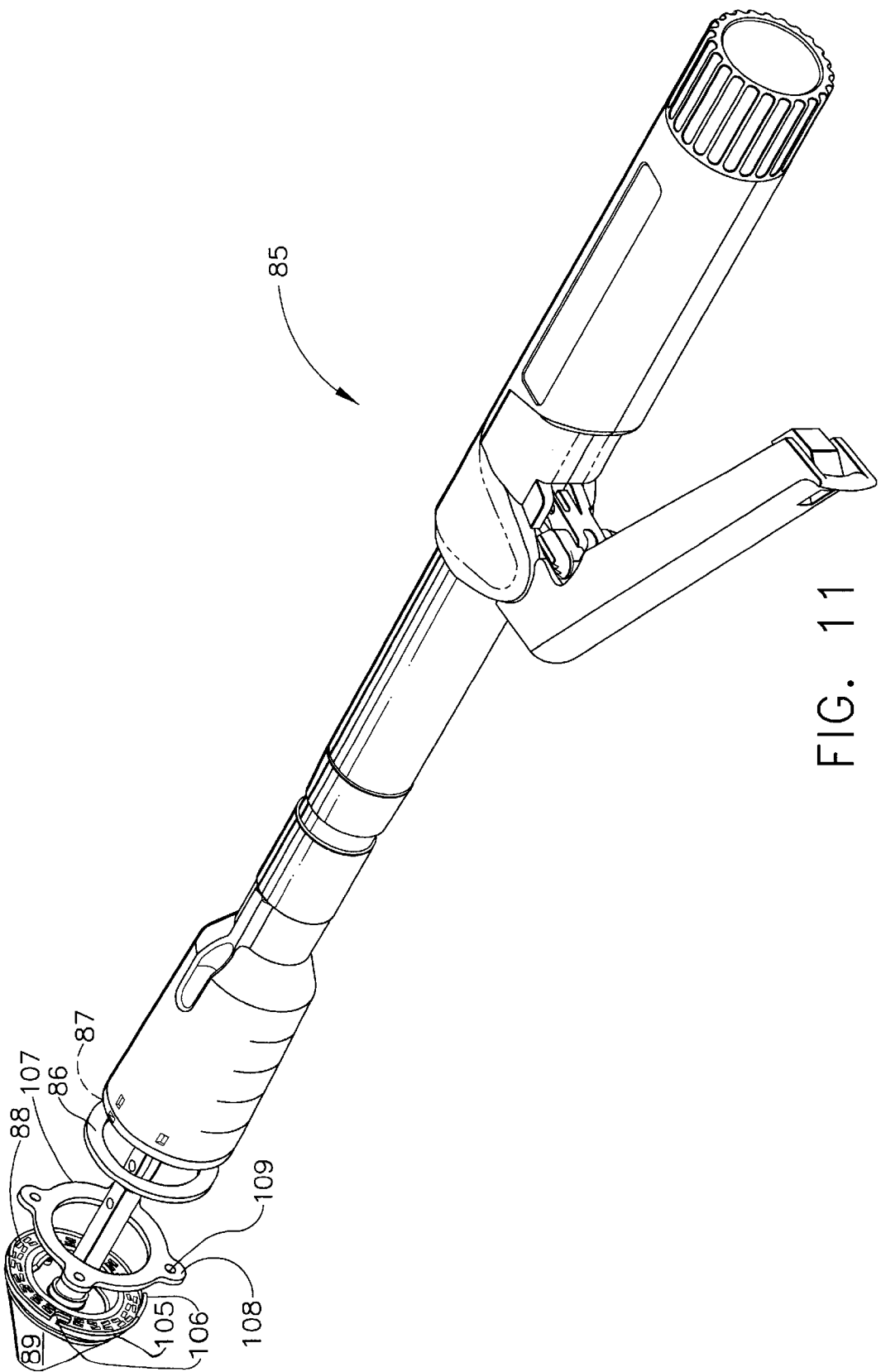

DEVICE FOR ATTACHMENT OF BUTTRESS MATERIAL TO A SURGICAL FASTENING DEVICE

FIELD OF THE INVENTION

The present invention relates, in general, to surgical fastening devices for applying a plurality of surgical fasteners into tissue and, more particularly, to a novel method of attaching a buttress material onto the surgical fastening device for the purpose of creating a reinforced surgical fastener line within tissue.

BACKGROUND OF THE INVENTION

Many surgical procedures involve the resection of tissue. One such procedure is lung volume reduction, which resects a portion of lung to treat emphysema. One problem encountered during the resection of body tissue, especially in conjunction with the use of staples, is the issue of hemostasis. Certain types of body tissue are more prone to the hemostasis issue such as the thin friable tissue found in the lung, and disease conditions can exacerbate the problems. Mechanical devices such as surgical staplers and linear cutters, both open and endoscopic, are utilized as a means of resecting diseased lung tissue. Staples provide hemostasis in vascular structures, and when applied to lung tissue, provide a good degree of pneumostasis as well. Surgical stapling instruments have a plurality of staples held in multiple staggered rows in a replaceable cartridge and a pair of opposed jaws of which at least one is moveable. The surgical stapling instruments compress the lung tissue between the cartridge and the jaw, and the staples are fired into the compressed tissue in close proximity to the diseased portion of the lung that is to be excised. A cutting blade is passed longitudinally between the innermost rows of formed staples, transecting the tissue. The surgical stapling device is removed from the surgical site, reloaded with another unfired stapling cartridge, and the procedure is repeated until the desired section of the lung is resected and removed. An example of an open linear cutter is given in U.S. Pat. No. 5,415,334 assigned to Ethicon Endo-Surgery, Cincinnati, Ohio on May 16, 1995, which is hereby incorporated herein by reference. An example of an endoscopic linear cutter is given in U.S. Pat. No. 5,597,107 assigned to Ethicon Endo-Surgery Cincinnati, Ohio on Jan. 28, 1997, which is hereby incorporated herein by reference.

One known problem with using surgical staplers used in this fashion has been the formation of air leaks in the stapled lung tissue. The leaks can occur in the cut line, and/or in the staple holes themselves. Frequently, the diseased lung tissue is thin and friable and can tear at the staples as the lungs re-inflate. These air leaks can be persistent and can extend the hospital stay for a patient by weeks. As a means to alleviate these leakage problems, surgeons reinforce the staple line by applying a buttress or pledget material to the desired stapling site and stapling through the buttress material. The buttress material provides reinforcement to the friable tissue. The tissue is compressed against the staple holes resulting in increased pneumostasis. This reduces the chances of tissue tearing at the staple line, and reduces staple pullout in friable tissue.

These reinforcement materials are typically releasably mounted onto the jaw members of a surgical stapling device such that upon firing, the reinforcement material is stapled to the lung tissue. Optimally the lung tissue is "sandwiched" between two layers of this reinforcement material. Alternately, buttress materials can be used in a number of other surgical procedures such as but not limited to; an ovarian hysterectomy, a gastric bypass, an anastomosis of intestinal tissue, or any other procedure that can require the reinforcement of a staple line or increased hemostasis in tissue.

Releasably attaching the buttress material to the jaw members of the surgical stapling device presents a special challenge. The buttress material must be fastened securely to the jaws of the surgical stapling device so that it won't fall off during normal operation, yet must be easily released from the surgical stapling device after the staples are fired. A variety of adhesive and mechanical attachment means are known. Both adhesive and mechanical attachment means are discussed below, and both have their deficiencies.

One example of a device which attaches a buttress material to a linear cutter with an adhesive is described in U.S. Pat. No. 5,441,193 and by Gravener et al. This device attaches buttress materials to a surgical instrument with a biocompatible cyanoacrylate adhesive. The adhesive bonding is applied along the edge portions of the buttress material and dashed lines of perforations are placed within the buttress material (adjacent to the glue line) so that the unglued central portion of buttress material can be torn from the glued edge portions. However, the portions of the buttress material having the adhesive applied thereto are not releasable from the device. As a consequence, removing the buttress from the instrument (after firing) can be especially difficult, as all of the material between the perforations must be torn simultaneously to release the surgical stapling device from tissue.

What is needed was an adhesive that would releasably attach the buttress material to the surgical device in a manner that makes it easier for the surgeon to remove the surgical device from the surgical site after firing. U.S. Pat. No. 5,752,965 by Francis et al. teaches the attaching the buttress material or strips to a surgical stapling device with a releasable adhesive that must be applied just prior to use. An alignment fixture is used to align the pair of buttress strips, adhesive is applied to the exposed surface of each buttress strip, and the jaws of the surgical stapling device are then closed upon the adhesive and buttress strips. When the jaws are opened, the buttress material is attached to the jaw and the cartridge of the surgical stapling device with the tacky liquid adhesive. The tacky liquid adhesive is taught as being composed of hydroxypropylmethyl cellulose, polypropylene glycol, and water. While attaching a buttress material in this manner may offer a releasable adhesive, the adhesive effects of the tacky liquid adhesive are temporary. In addition, the attachment process is time consuming, and the attachment step must be repeated for each firing. Lastly, once the tacky adhesive is exposed to air, volatile elements of the adhesive begin to evaporate. This limits the application of this tacky adhesive to just prior to or during surgery.

What is needed is a releasable adhesive that that won't dry out or degrade over time. Such an adhesive would enable the buttress material to be attached to the surgical stapling device at the manufacturing plant, and would result in both time and cost savings. European patent application EP 1064883A1 by Leslie Hamilton et al. teaches a releasable adhesive of nontoxic bioabsorbable aliphatic ester polymers that are semi-crystalline solids or tacky liquids (of honey-like consistency). The adhesive is characterized by being flowable at body temperatures (37° C.) and preferably flowable at room temperatures (25° C.). However, the adhesive may become much more fluid at the elevated temperatures (up to 50° C.) frequently encountered in trucks, shipping containers, railroad cars, and warehouses. Under the elevated temperature conditions, the adhesive can migrate to other parts of the instrument or instrument packaging and the migration can reduce the strength of the adhesive bond.

As seen from the above discussion, attaching a buttress material to a surgical stapler with an adhesive can present many problems. Mechanical attachment of buttress material to a surgical stapling device is also well known in the art and avoids the issues found with adhesives. Many methods of mechanical attachment exist, and a common one is the placement of a sleeve over the clamping members of the surgical stapling device. The sleeves can be formed from flexible fabric such as buttress material, or can contain a releasable strip of buttress material attached to a different fabric. Many of these sleeves are described in U.S. Pat. No. 5,503,638 by Cooper et al, in U.S. Pat. No. 5,702,409 by Rayburn et al., in U.S. Pat. No. 5,810,855 by Rayburn et al., and in U.S. Pat. No. 5,964,774 by McKean et al.

While sleeves can effectively be used to attach the buttress material to the end effector of the surgical stapling device, sleeves can cause other complications during surgery. For example, if the sleeve is formed from a solid sleeve of buttress material, firing the surgical stapling device staples the buttress and tissue and severs the buttress sleeve and tissue between the staple lines. This action leaves the portions of tissue (on either side of the cut line) attached together by a sheet of buttress material. This requires the surgeon to go in and sever the cut sleeve of buttress to separate the severed tissue, and remove any unwanted portion of the buttress material.

What is needed is a means of releasably attaching a buttress strip onto a surgical stapling device, that remains effective over a long period of time, remains operational at all temperatures that are likely to be encountered by the product, and is easily released from the surgical stapling device.

SUMMARY OF THE INVENTION

In accordance with the present invention, an assembly for releasably attaching a buttress material onto a tissue clamping member of a surgical stapling device is disclosed. The assembly has a substantially rigid frame for connecting to a top surface of a tissue clamping member of a surgical stapling device when the assembly is disposed thereon. A buttress material is attached to first and second sides of the frame for abutting against a bottom surface of a tissue clamping member of a surgical stapling device when the assembly is disposed thereon.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6 is an isometric view of a surgical stapling device showing an end effector having buttress strips releasably attached to a first clamping surface of an anvil by an anvil carrier, the buttress strip being removable by distal motion relative to the surgical stapling device;

FIG. 9 is a distal end view of an alternate assembly of the elements of the anvil carrier;

FIG. 11 is an isometric view of a circular stapling instrument with an anvil in the open position and an attachment ring attached to the anvil, wherein a perforated buttress ring is being removably and rotatably attached onto the attachment ring.

DETAILED DESCRIPTION OF THE INVENTION

Figure 1:
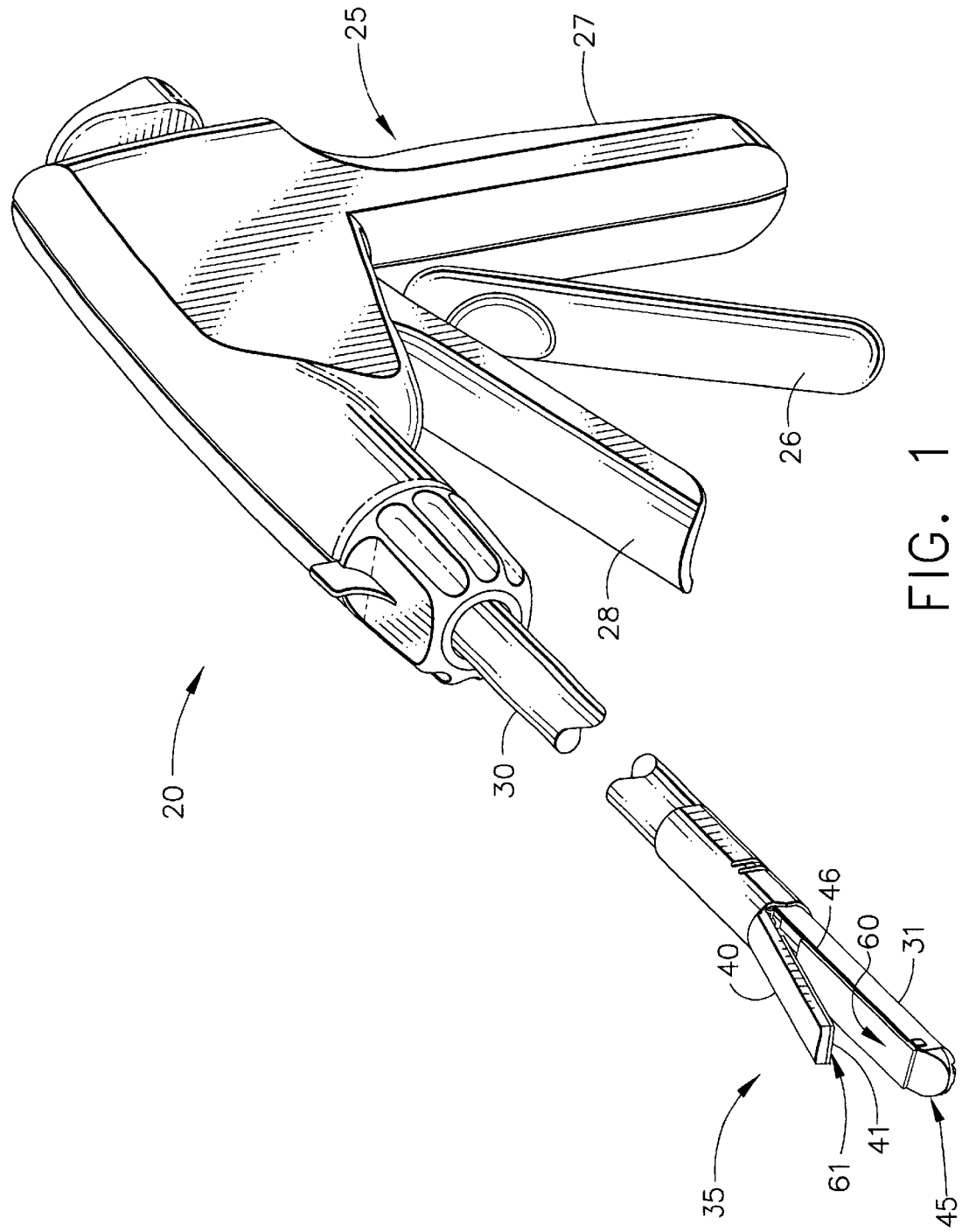
FIG. 1 is an isometric view of a surgical stapling device showing an end effector having buttress strips releasably attached to a first clamping surface of an anvil and releasably attached to a second clamping surface of a staple cartridge by a hot melt adhesive of the present invention.

Referring now to the figures in which like numerals indicate the same element throughout the views, FIGS. 6 shows a surgical stapling device 20 made in accordance with the present invention. Device 20 has an anvil carrier 90 of the present invention releasably attaching a perforated buttress strip 101 to the end effector 35. The surgical stapling device 20 shown is an endocutter and is well known in the art for clamping, stapling, and cutting body tissue. Alternately, the surgical stapling device 20 can be one of a number of other fastening devices such as a circular stapler, a stapler, a clip applier, or any one of a number of other fastening or stapling devices capable of single or multiple firings. The staples or fasteners can be contained within a staple cartridge formed integrally with the surgical stapling device, or within a removable staple cartridge that can be fired and replaced allowing multiple firings from the same surgical fastening device. The assembly of the present invention is illustrated in FIGS. 6–11.

Surgical stapling device 20 has a handle 25 for the operator to grasp, an elongated shaft 30 extending distally from the handle 25, and end effector 35 extending distally from the shaft 30. End effector 35 has a first and a second tissue clamping member, at least one of which is movable between an open position for receiving tissue therebetween, and a closed position for stapling tissue therebetween. The first tissue clamping member has a fixed channel 31 extending from the shaft 30 and a removable staple cartridge 45 mounted therein. The second tissue clamping member is a moveable anvil 40 which is opposite to the first tissue clamping member. Staple cartridge 45 is shown placed within the fixed channel 31 and contains a plurality of staples 49 housed within. Moveable anvil 40 is operably attached to a closure trigger 26 extending from the handle 25 and moves in response to movement of the closure trigger 26. Moving the closure trigger 26 from the open position shown in FIG. 6 towards a grip 27 of the handle 25 moves the anvil 40 from the open position of FIG. 6 to a closed position adjacent to the removable staple cartridge 45 (not shown). Movement of a firing trigger 28 towards the closure trigger 26 (when closure trigger 26 and anvil 40 are in the closed position) expels the plurality of staples 49 contained within the removable staple cartridge 45. The staples 49 are driven from the removable staple cartridge 45, through the buttress strips 60 and 61, and are formed into tight "B" shapes (not shown) against the anvil 40. An example of the surgical stapling device 20 is the TSB35 Endopath™ ETS Endoscopic Linear Cutter by Ethicon-Endo Surgery, 4545 Creek Road, Cincinnati Ohio. The surgical stapling device 20 and removable staple cartridge 45 are generally described in a commonly assigned U.S. Pat. No. 5,597,107, which is incorporated herein by reference.

As shown in FIG. 6, the first buttress strip 60 is releasably attached to a first tissue clamping surface 46 of the removable staple cartridge 45. The buttress strip 60 can be formed from a wide variety of buttress materials including VICRYL®, produced by Ethicon, Inc., Somerville N.J., "DEXON®, produced by Sherwood-Davis and Geck, St. Louis, Mo., and TEFLON®, produced by E. I. DuPont de Nemours & Co., Wilmington, Del. Additionally, other materials include animal material such as tanned bovine pericardium, biocompatable elastomers such as ε-caprolactone glycolide produced by Ethicon Inc., Gargrave, England, or any one of a number of suitable buttress materials. Suitable ε-caprolactone glycolide materials or foams are of special interest and are described in U.S. Pat. No. 5,468,253 hereby incorporated by reference. It is an object of the present invention to releasably attach the buttress strips 60 and 61 to at least a portion the surgical stapling device 20 for long periods of time, up to two or more years.

Attachment of Buttress Strips with A Hot Melt Adhesive

Figure 2:
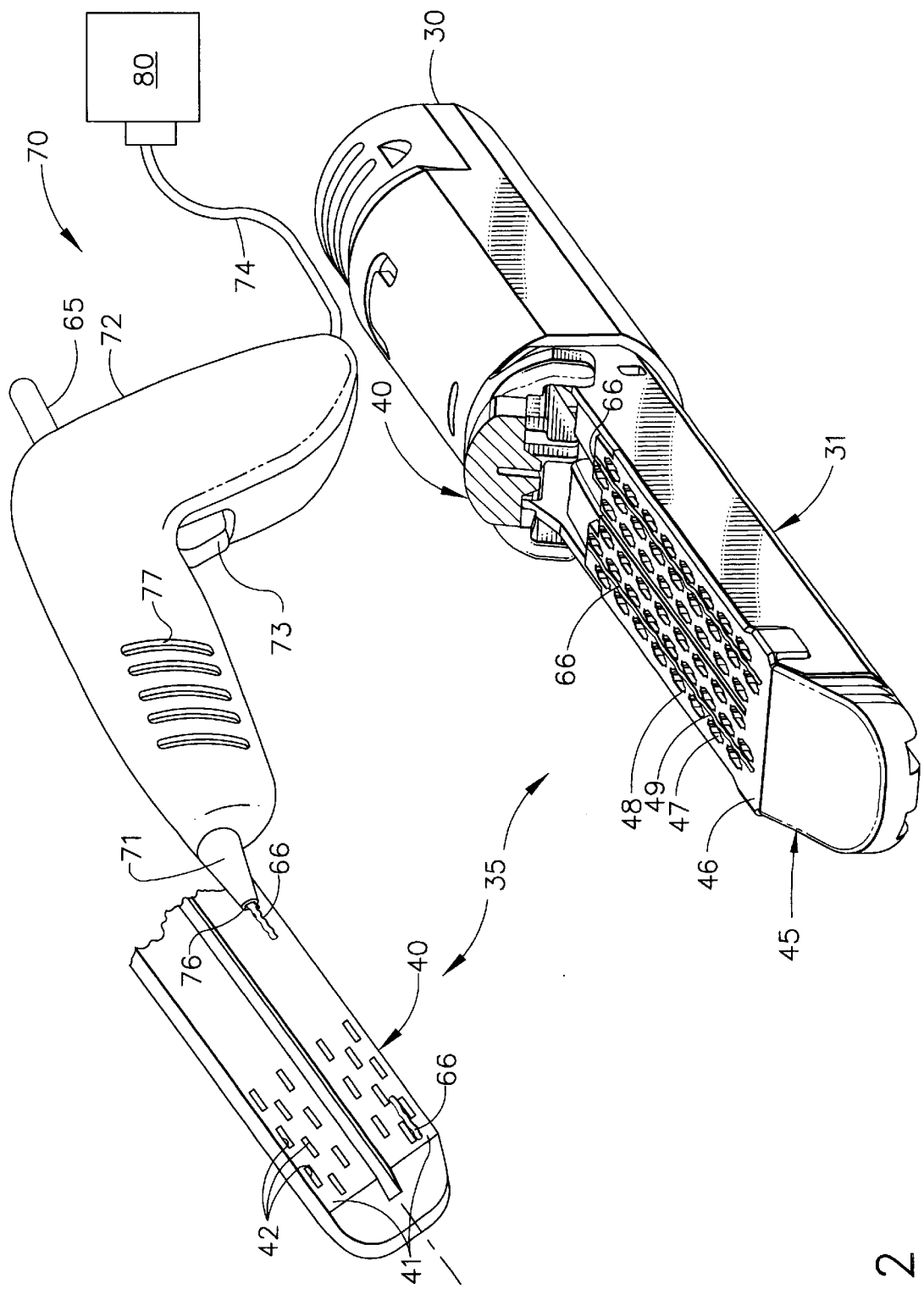
FIG. 2 is an enlarged isometric view of the end effector of the surgical stapling device of FIG. 1 with the anvil sectioned and rotated for clarity, the view showing the step of applying the molten hot melt adhesive of the present invention onto the first and second clamping surfaces of the end effector with an applicator.
Figure 3:
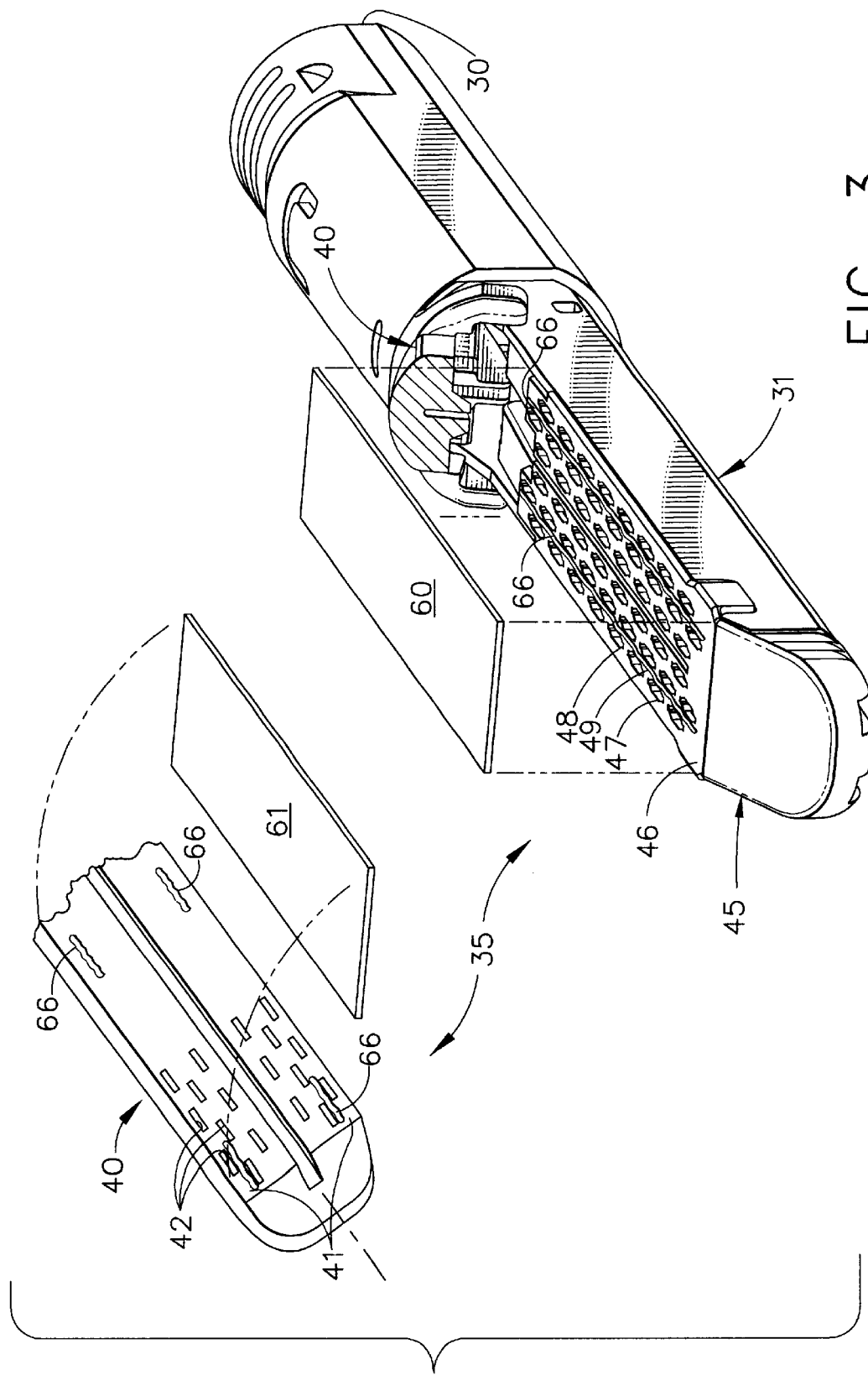
FIG. 3 is an enlarged isometric view of the end effector of the surgical stapling device with the anvil sectioned and rotated for clarity, the view showing the step of attaching a strip of buttress material onto each of the tissue clamping surfaces by placing the buttress material into contact with molten hot melt adhesive of the present invention placed thereon.
Figure 4:
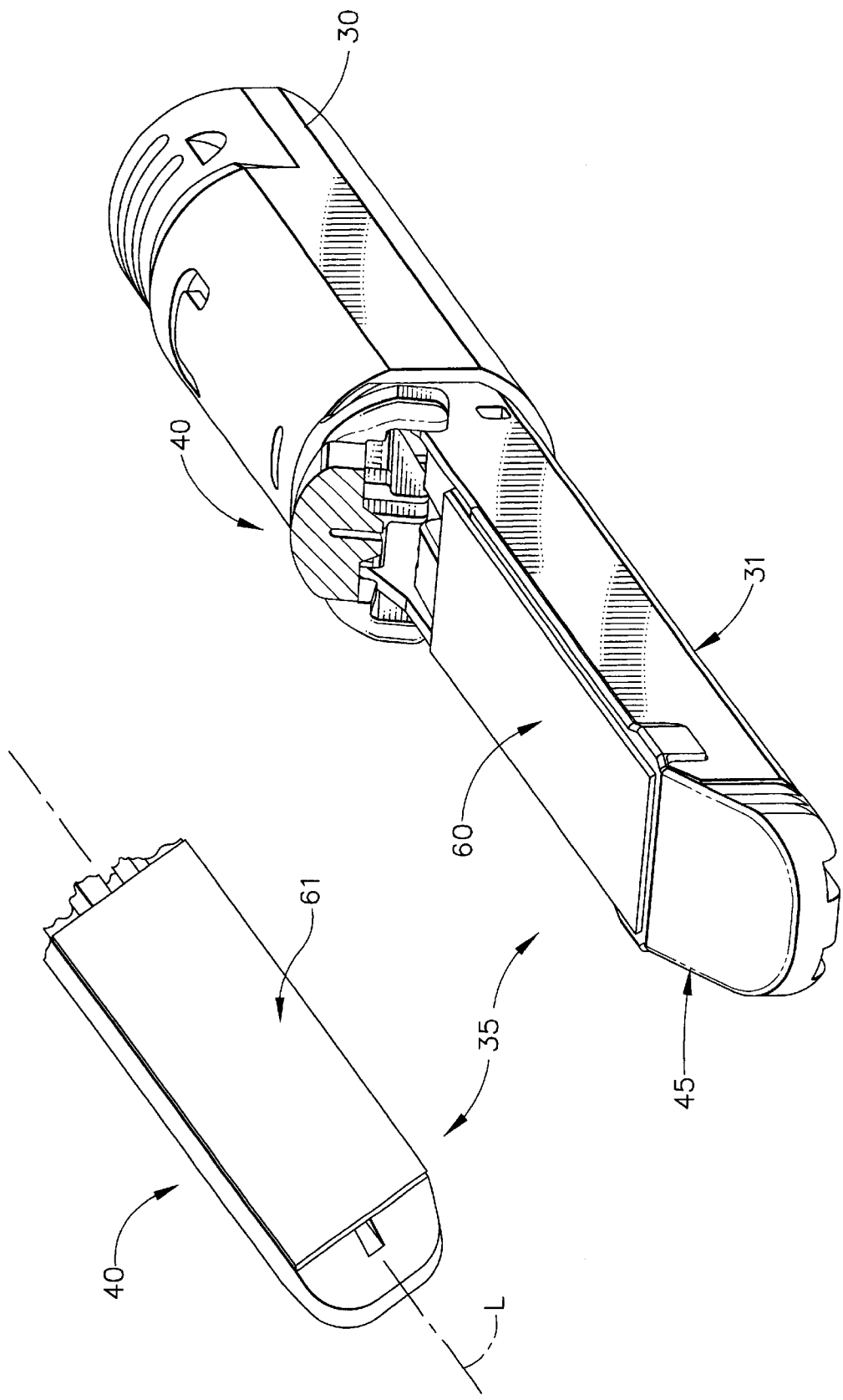
FIG. 4 is an isometric exploded view of the step of cooling the hot melt adhesive of the present invention past a set point, the releasable adhesive becoming a solid and adhering each of the portions of buttress material to each of the respective tissue clamping surfaces.

FIGS. 2–4 shows the steps of releasably attaching buttress strips 60 and 61 to the first and second tissue clamping surfaces 46,41 of the end effector 35 respectively, with a solid adhesive 65 of the present invention. Solid adhesive 65 is a solid at room temperatures (25° C.), a solid at body temperatures (37°), and meltable at elevated temperatures. Adhesives of this type are called hot melt adhesives, and are applied as a molten adhesive 66 during the gluing process. When the molten adhesive 66 cools, it reverts back into the solid adhesive 65, forming an adhesive bond. In FIGS. 2–4, the end effector 35 of the surgical stapling device 20 is shown enlarged, and the anvil 40 is shown sectioned and rotated for clarity. Alternately, the hot melt adhesive 65 can be melted by a solvent and used to adhere buttress strips 60,61 to the surgical stapling device 20. When the solvent evaporates from the molten adhesive 66, it reverts back to the solid hot melt adhesive 65 and attaches the buttress strips 60,61 to the surgical stapling device 20.

FIG. 2 shows the first step of applying the molten adhesive 66 to the first and second clamping surfaces 46,41 with an applicator 70. The applicator 70 has a handle 72, a distal nozzle 71 for the disbursement of molten adhesive 66, a resistive heating device 75 (not shown) contained within the handle 72 to melt the a distal end of the solid adhesive 65, and an electrical cord 74. Attachment of the electrical cord 74 to a power supply 80 engages the resistive heating device 75. Handle 72 has cooling slots 77 adjacent to the resistive heating device 75 to prevent overheating. These types of glue or adhesive applicators 70 are well known in the art as hot melt glue guns and are readily available for commercial or home use. An excellent example of a hot melt glue gun or adhesive applicator 70 is the SHURE BONDER® Pro 9000 glue gun made by FPL Corporation, Wauconda, Ill., 60084.

In FIG. 2, a rod of solid adhesive 65 is shown inserted into an opening at the proximal end of the handle 72. As the rod of solid adhesive 65 is inserted, it operably engages a feeding mechanism (not shown) that is operably coupled to the applicator trigger 73. Actuation of the applicator trigger 73 moves the rod of solid adhesive 65 distally within the handle until it contacts the hot resistive heating device 75 and melts the distal portion of the rod of solid adhesive 65. Applying additional pressure on the applicator trigger 73 forces the molten adhesive 66 from an orifice 76 of the nozzle 71 and moves the rod of solid adhesive 65 distally into the applicator 70. Whereas the hot melt glue gun or applicator 70 is the preferred method of applying the solid adhesive 65, alternate adhesive appliers are available. These alternate adhesive appliers include but are not limited to a pressurized molten glue dispenser that applies a molten ribbon of adhesive, a sprayer that applies a spray of molten droplets, and a hot roller that applies a film of molten adhesive.

In FIG. 2, the applicator 70 is shown applying several lines of molten adhesive 66 onto the first and second tissue clamping surfaces 46, 41 of the anvil 40 and cartridge 45. The molten adhesive is applied to these surfaces prior to the step of applying the buttress strips 60 and 61. The molten adhesive 66 is shown being applied onto the second tissue clamping surface 41 between the staple pockets 42 embossed therein. The two lines of molten adhesive 66 are kept short on the second tissue clamping surface 41 and provide enough retention force to attach the first buttress strip 60 onto the second tissue clamping surface 41, yet enable the first buttress strip 60 to be easily removed.

Two longer rows of molten adhesive 66 are shown placed upon the first clamping surface 46 of the removable staple cartridge 45, between longitudinal rows of staple slots 47. Each staple slot 47 has a piston-like staple driver 48 (not shown) moveable from a first recessed position deep within the removable staple cartridge 45 to a second position extending from the first tissue clamping surface 46. In FIGS. 2 and 3, the staple drivers 48 are in the first recessed position deep within the staple slots 47 of the removable staple cartridge 45. A "U" shaped staple 49 (not shown) is placed within each staple slot 47, on top of the staple drivers 48 recessed therein. Movement of the staple drivers 48 to the second position ejects the staples 49 from the removable cartridge 45. In these Figures, the staple drivers 48 and staples 49 are recessed within the staple slots 47 and cannot be seen. Staple cartridges 45 and movement of the staple drivers 48 and staples 49 are well known in the art and can be found in U.S. Pat. No. 5,415,334 by Williamson, IV et al., which is incorporated herein by reference.

As shown in FIG. 3, once the molten adhesive 66 is applied, the second step is to apply the buttress strips 60 and 61 onto their respective tissue clamping surfaces 46,41. The first and second buttress strips 60 and 61 are shown moving towards the first and second tissue clamping surfaces 46,41 and the molten adhesive 66. FIG. 4 shows the last step of the gluing process where the buttress strips 60 and 61 are placed into position, and pressed onto the respective clamping surfaces 46,41. As the buttress strips 60, 61 are pressed into place, the molten adhesive 66 is compressed between the buttress strips 61 and the clamping surfaces 46,41, and allowed to cool back into the solid adhesive 65, attaching the buttress 60,61 to the surgical stapling device 20.

Firing the surgical stapling device 20 moves the staple drivers 48 from the first position within the cartridge 45 to the second position, i.e. extended from the first tissue clamping surface 46. This action simultaneously lifts and forms the staples 49 against the anvil 40 and lifts the first buttress strip 60 upwardly and away from the first tissue clamping surface 46 of the cartridge 45. The upwards movement of the first buttress strip 60 breaks the adhesive bond between the first buttress strip 60 and the first tissue clamping surface 46, releasing the first buttress strip 61 from the staple cartridge 45.

Alternately, the buttress strip 61 can be adhered to the cartridge 45 by generally placing the molten adhesive 66 into the staple slots 47 and attaching the first buttress strip 60 onto the cartridge 45. The molten adhesive can be placed into the staple slots 47 in two different ways. First, the hot melt can be injected directly into the staple slots 47 with the hot melt glue gun, adhering the buttress strip 60 to the staple slot 47 (not shown). Second, the molten adhesive 66 can enter the staple pockets 48 by placing the molten adhesive 66 onto the first tissue clamping surface 46 adjacent to the staple slot 47 (FIG. 3), and forcing it into the staple pockets 48 by pressing the first buttress strip 60 against the first clamping surface 46. The act of pressing forces some of the molten adhesive 66 from the first tissue clamping surface 46 and into the adjacent staple slots 47, adhering the buttress 61 to both the staple slots 47 and the first tissue clamping surface 46 (not shown). When solid adhesive 65 is within the staple slots 47 and the surgical stapling device 20 is fired, the staple drivers 48 and staples 49 move upwardly within the staple slots 47 and contact the solid adhesive 65 therein. The contact with the moving staple drivers 48 and staples 49 ejects the solid adhesive 65 from the slots 47 and breaks the adhesive bond between the first buttress strip 60 and the removable staple cartridge 45.

Thus, the solid adhesive 65 of the present invention becomes a releasable adhesive when the firing of the surgical stapling instrument 20 is used to break the adhesive bond between the staple cartridge 45 and the first buttress strip 60. It is important to note that using the firing of the stapling device 20 to break an adhesive bond is not dependent on the adhesive composition. That is, a wide variety of adhesives can be released in the manners described above. In addition to hot melt adhesives, other adhesives can be applied at room temperatures and can include adhesives such as elastomeric compounds, RTV silicones, natural and synthetic rubbers, anaerobic compounds, sealants, moldable compounds such as dental dam compounds, or maleable materials such as waxes. Additionally, the above adhesives or any one of a number of other adhesives such as acrylics, cyanoacrylates, epoxies and the like can be used with a bonding inhibitor. The bonding inhibitors act as a barrier to reduce the strength of the adhesive bond and can include oils, greases, waxes, mold releases, Teflon's, silicones or any other surface contaminant that inhibits the adhesive bonding strength.

The ejection of the staples 49 from the removable staple cartridge 45 also releases the second buttress strip 61 from the second tissue clamping surface 41 and forms the "U" shaped staples 49 into "B" shapes. The "U" shaped staples 49 are formed into "B" shapes by driving them through the second buttress strip 62 attached to the second tissue clamping surface 41 and against the staple pockets 42 within the anvil 40. As the wire of the staple 49 is driven into the staple pocket 42, the ends of the staple wire curl around into the "B" shape, and dislodge the solid adhesive 65 from the staple pockets 42 and the second tissue clamping surface 41. This action detaches the second buttress strip 61 from the anvil 40 (not shown).

Figure 5:
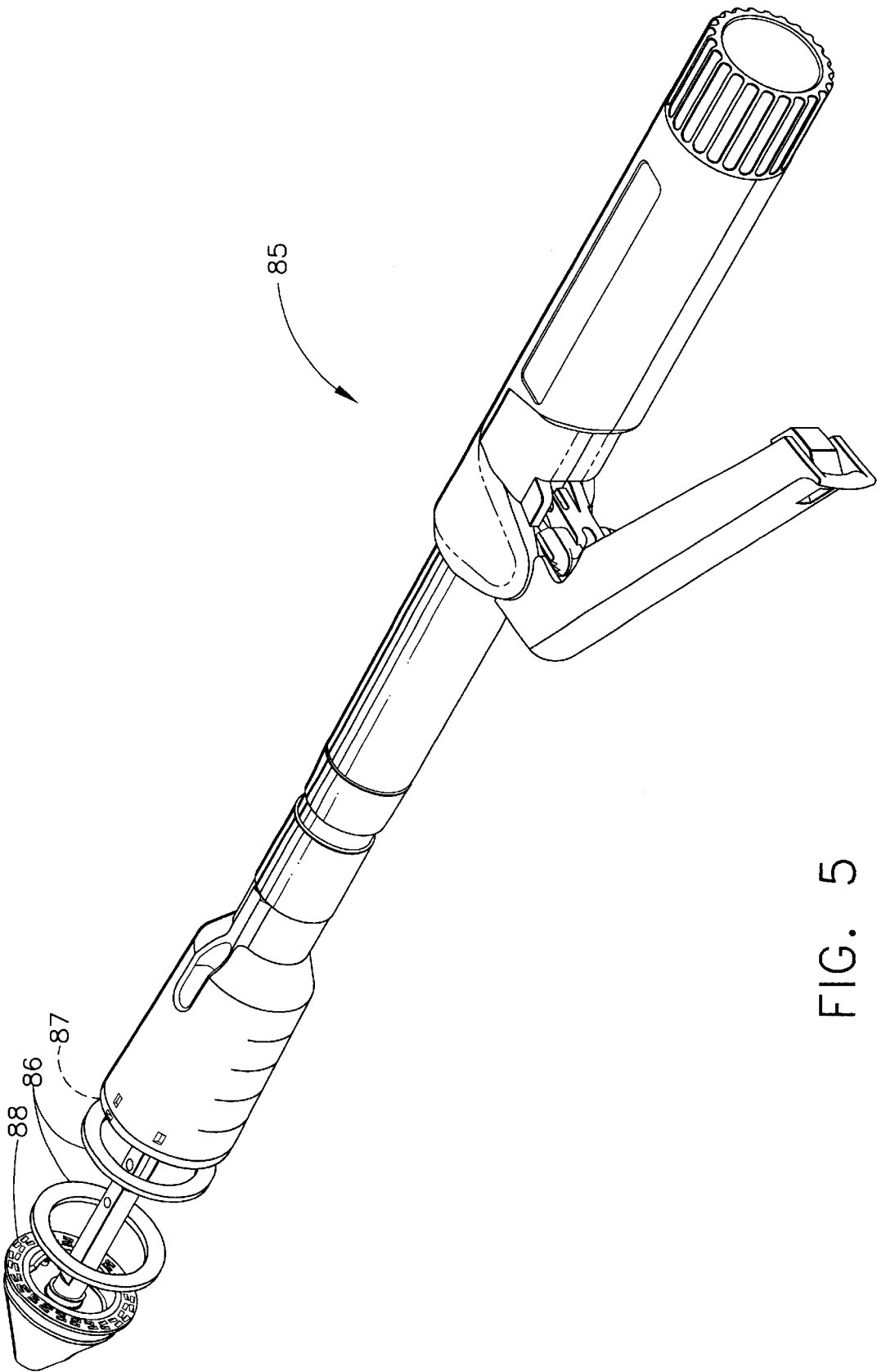
FIG. 5 is an isometric view of a circular stapling instrument showing buttress rings placed thereon prior to the step of applying the molten adhesive of the present invention onto an anvil and staple cartridge of the circular stapling instrument for the attachment of the buttress rings thereto.

FIG. 5 shows molten adhesive 66 being used to attach buttress materials to a circular stapler 85. Buttress rings 86 are shown exploded away from a first and a second circular compression surfaces 87,88 just prior to the step of gluing the buttress rings 86 onto the circular compression surfaces 88,87 with molten adhesive 66. In FIG. 5, the molten adhesive 66 is applied onto the first compression surface 87 and is hidden.

The Hot Melt Adhesive Composition

The solid adhesive 65 can be any one of a variety of hot melt adhesives that are commercially available. It is preferable that the hot melt adhesive be biocompatible with body tissue and can be natural or synthetic. Natural biological polymers, and in particular a number of biological proteins can be used as hot melt adhesives. These proteins can include collagen, gelatin, fibrin, fibronectin, fibrinogen, elastin, serum albumin, hemoglobin, ovalbumin and the like or any combination thereof. Additionally, polysaccharides such as hyaluronic acid, chondroitin sulfate, hydroxyethyl starch, hydroxyethyl cellulose, hydroxypropyl-cellulose, carboxyetyl-cellulose, chitan/chitosan, agarose and alginate may be used alone or in combination with other materials.

Synthetic materials can include poly (lactic acid), poly (glycolic acid) poly (hydroxybutyrate), poly (phosphazine), polyester, polyethylene glycol, polyethylene oxide, polyacrylamide, polyhydroxyethylmethylacrylate, polyvinypyrrolidon, polyvinyl alcohol, polyacrylic acid, polyacetate, polycaprolactone, polypropelene, nylon and the like. Also, suitable biocompatible, bioabsorbable polymers can also include but are not limited to polymers selected from the group consisting of aliphatic polyesters, poly (amino acids), copoly (ether-esters), polyalkylenes oxalates, polyamides, tyrosine derived polycarbonates, poly (iminocarbonates), polyorthoesters, polyoxaesters, polyarnidoesters, polyoxaesters containing amine groups, poly (anhydrides), polyphosphazenes, biomolecules (i.e., biopolymers such as collagen, elastin, bioabsorbable starches, etc.) and blends thereof Of special interest for the solid adhesive 65 is a copolymer that is a solid at temperatures generally below 40° C. The preferred copolymer is a copolymer of $\epsilon$-caprolactone or trimethylene carbonate and glycolide. Most preferably, the copolymer is a copolymer of $\epsilon$-caprolactone and glycolide. The amount of $\epsilon$-caprolactone can be between 30 and 45 mole percent with the balance being glycolide. Ideally, the copolymer can be composed of 36:64 (mol/mol) [poly ($\epsilon$-caprolactone-co-glycolide)]. The copolymer is an elastomeric containing less than one percent of unreacted monomer as determined by proton NMR spectography. The inherent viscosity is determined in a 0.1 g/dL solution of hexaflouroisopropanol (HFIP) at 25° C., and can range from about 0.8 g/dL to about 3.2 g/dL, preferably from about 0.6 g/dL to about 2.4 g/dL, and most preferably at about 1.6 g/dL. In an especially preferred embodiment, both the preferred solid adhesive and the preferred buttress material can be formed from the same bioabsorbable material, ϵ-caprolactone glycolide.

The solid adhesive 65 can be characterized as being a solid at temperatures up to 40° C. and melts without degradation at elevated temperatures between 40.1° C. to 600° C. More preferred are solid adhesives 65 that melt without degradation at elevated temperatures between 120° C. to 240° C. and most preferably at 180° C. The copolymer described above can be prepared in accordance with the descriptions provided in U.S. Pat. Nos. 5,468,253, 5,133,739, and 4,605,730, each of which is incorporated by reference.

Alternate Device and Method for Attaching Buttress Strips to an Anvil

FIGS. 6–11 illustrate another device and method for attaching a buttress strip onto an anvil 40 of the surgical stapling device 20 of FIG. 1. FIG. 6 shows the surgical stapling device 20 with an anvil carrier 90 secured to the anvil 40, and a buttress strip removably attached to the anvil carrier 90. Anvil carrier 90 slides onto the anvil 40 and locks onto the anvil 40 when fully mounted. The lock can be easily disengaged for removal or replacement of the anvil carrier 90.

Figure 7:
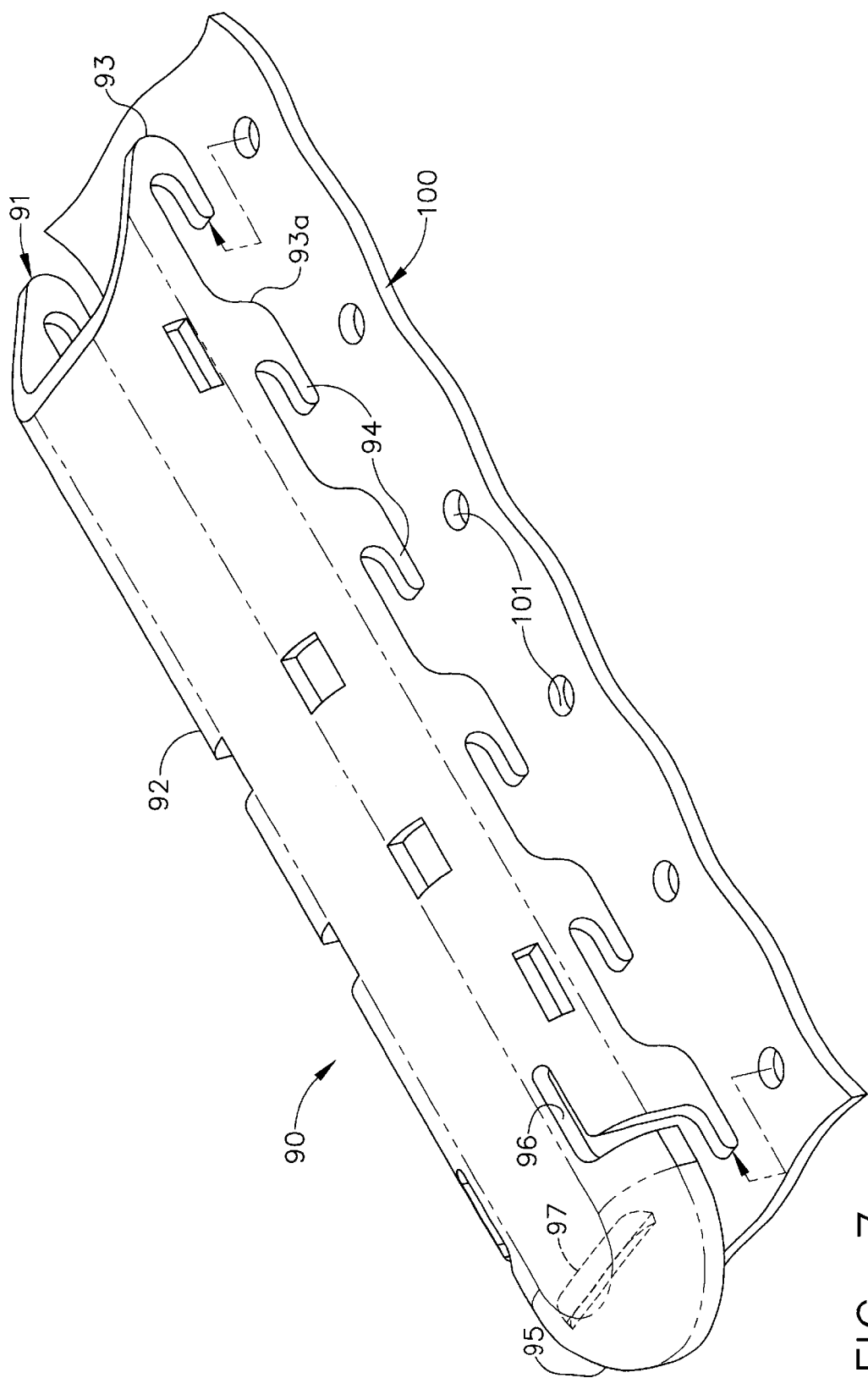
FIG. 7 is an isometric exploded view of the elements of the anvil carrier showing the path of a perforated buttress strip as it is releasably assembled with a carrier shell.
Figure 8:
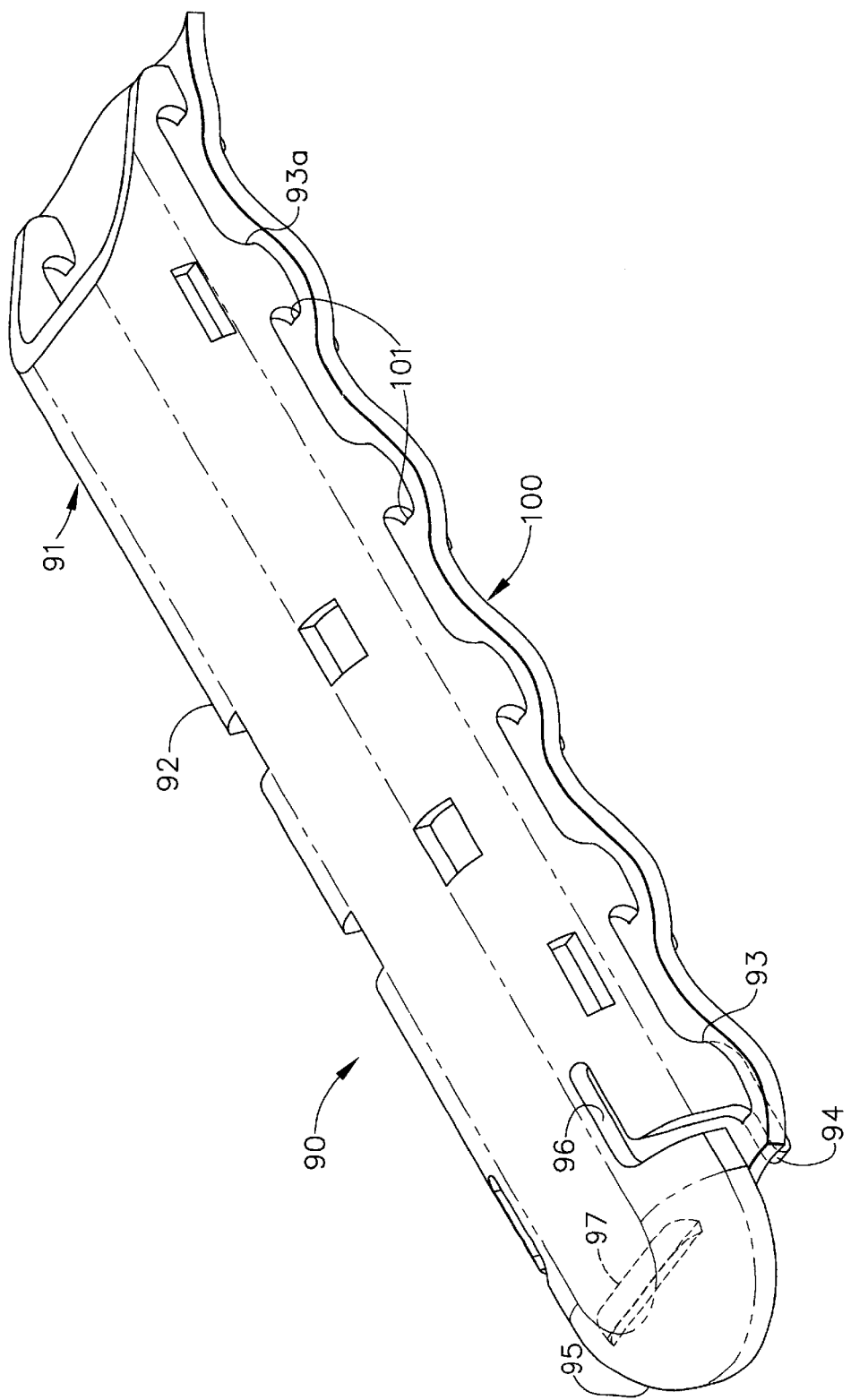
FIG. 8 is an isometric view of the assembled elements of the anvil carrier of FIG. 7.

As best shown in FIGS. 7–9, the anvil carrier 90 is assembled from a frame or carrier shell 91 and a perforated buttress strip 100. Carrier shell 91 is hollow, is conformed to slip over the anvil 40, has an inverted "U" shaped carrier body 92, and has a nose 95 extending distally therefrom. Nose 95 can be blunt or atraumatic to prevent tissue damage during placement of the surgical stapling device 20 at the surgical site. A spring member 96 connects nose 95 to a distal end of the carrier body 92. A lock or retention feature 97 is located on an inner surface (not shown) of the nose 95 to releasably engage the anvil carrier 90 with the anvil 40 of the surgical stapling device 20. The retention feature 97 can be a convex dimple or rib that engages with a concave mating feature (not shown) on the anvil 40 of the surgical stapling device 20. Lifting the nose 95 away from the anvil 40 (when the retention feature 97 is engaged with the anvil 40) deflects the spring member 96, lifts the retention feature 97 from the concave mating feature on the anvil 40, and unlocks the carrier shell from the anvil 40. A plurality of attachment features, such as "L" shaped hooks 93, extend downwardly on each side of the carrier body 92, with arms 94 extending horizontally in the distal direction from a vertical portion or first member 93a of the "L" shaped hooks 93. Whereas hooks 93 are the preferred embodiment, spikes, arms, tabs, bosses or any one of a number of releasable means can be added to the carrier shell 91. Carrier shell 91 can be made from a rigid or semi-rigid material such as an engineering plastic, examples of which can include liquid crystal polymers, polycarbonates, polystyrenes, or any one of a number of suitable medical grades of engineering thermoform plastics or thermoset plastics. Additionally, the carrier shell 91 can also be formed from any metallic material such as aluminum, steel, stainless steel, copper, or combinations and alloys thereof.

Perforated buttress strip 100 is a rectangular sheet formed from any of the buttress materials described above, and has rows of spaced-apart openings 101 extending therethrough. Perforated buttress strip 100 is attached onto the carrier shell 91 by threading each horizontal arm 94 fully into each respective opening 101 within the perforated buttress strip 100 until the openings 101 are brought into contact with the first member 93a or vertical portion of the "L" shaped hooks 93. Moving the perforated buttress strip 100 distally relative to the carrier shell 91, moves the openings 101 off of the arms 94 and releases the perforated buttress strip 100 from the carrier shell 91. Thus, the perforated buttress strip 100 is detachable from the carrier shell 91 by linear motion in one direction. Arrows are provided in FIG. 7 to show the path of the openings 101 as the perforated buttress strip 100 is threaded onto the arms 94.

FIG. 8 is an isometric view showing the preferred assembly of the perforated buttress strip 100 with the carrier shell 91. In this assembly, each of the arms 94 of the hooks 93 are shown placed into their respective openings 100 within perforated buttress strip 100. When the arms 94 are assembled with the openings 101, a slight dimpling occurs at the edges of the perforated buttress 100 from the placement of the arms 94 into the openings 101. When the preferred assembly of the anvil carrier 90 is installed onto the anvil 40, the perforated buttress strip 100 is tented away from the carrier shell 91 by the second clamping surface 41 of the anvil 40, flattening the perforated buttress strip 100.

FIG. 9 is a cross sectional view of an alternate assembly of the perforated buttress strip 100 with the carrier shell 91. In this Figure, the edges of the perforated buttress strip 100 are folded upwardly along each row of openings 101 into a general "U" shape. The vertical sides of the "U" shaped perforated buttress 101 are then placed inside of the hooks 93, and each of the arms 94 are threaded into their respective openings 101. This attachment method produces a generally flat horizontal section on the attached perforated buttress strip 100.

During surgery, the anvil carrier 90 is used in the following manner. The anvil carrier 90 (containing a perforated buttress strip 100) is slid onto the open anvil 40 of the surgical stapling device 20. Next, the anvil 40 is closed and the end effector 35 of the surgical stapling device 20 is inserted into the patient. The anvil 40 is opened and the end effector is placed onto tissue at a selected surgical site. Anvil 40 is closed to clamp tissue between a second clamping surface 41 on the anvil 40 and a first clamping surface 46 on the removable staple cartridge 45. The surgical stapling device 20 is fired, stapling the perforated buttress strip 100 onto tissue and severing the tissue and buttress between the staple lines. The anvil 40 is opened, and the surgical stapling device 20 is withdrawn proximally away from the surgical site. As the surgical stapling device 20 is withdrawn, the stapled perforated buttress strip 100 remains attached to tissue and the arms 94 of the carrier shell 91 slip out of the openings 101 within the perforated buttress strip 100, releasing the perforated buttress strip 100 from the surgical stapling device 20. To reload the surgical stapling device 20 with a fresh anvil carrier 90, the surgeon must remove the surgical stapling device 20 from the patient. Next, the surgeon removes the spent carrier shell 91 from the anvil 40 by lifting the nose 95 to unlock the retention feature 97 from the anvil 40 and slides the carrier shell 91 off of the anvil 40. A fresh anvil carrier 90 is slid onto the anvil 40 to finish the reloading process.

Figure 10:
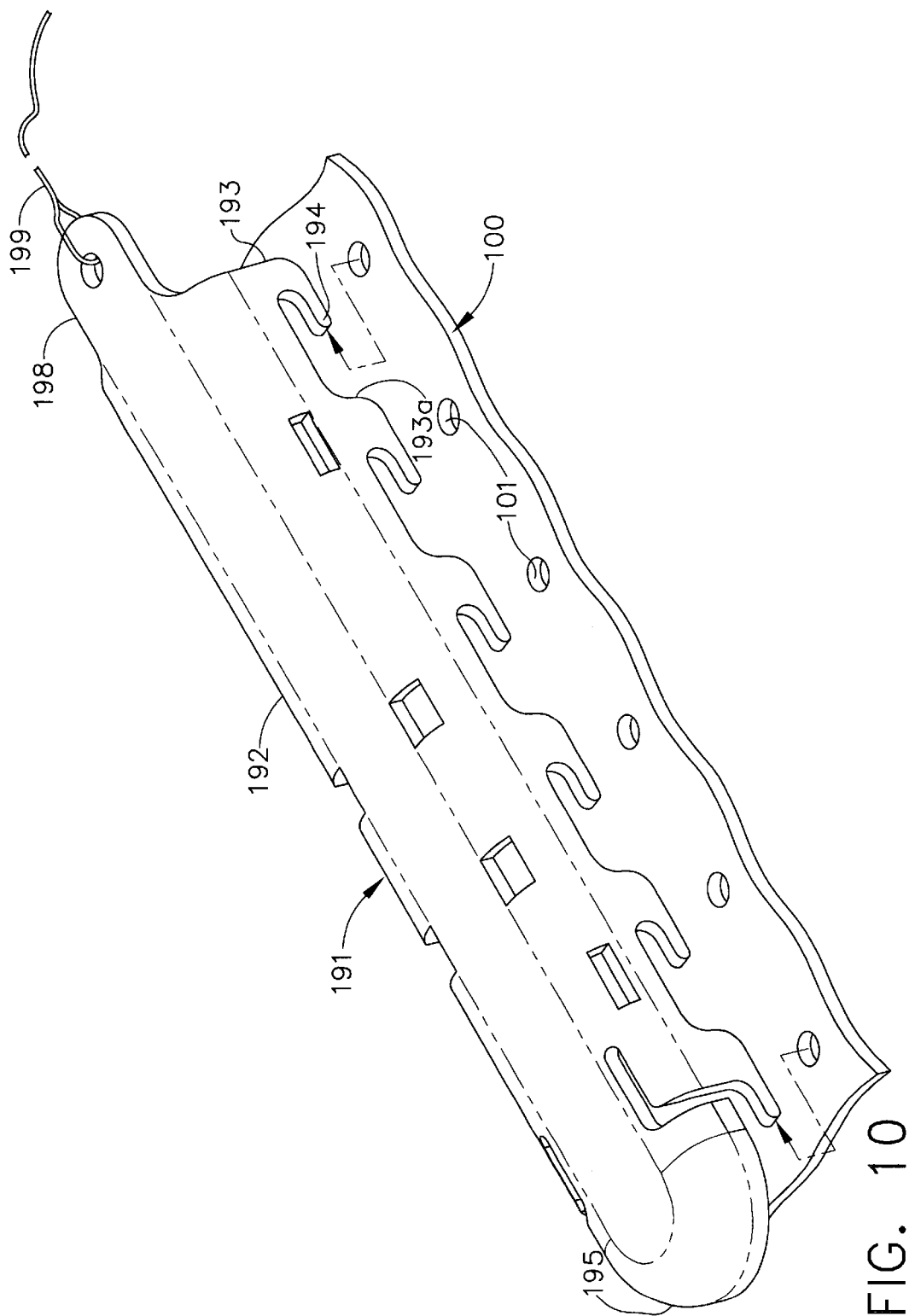
FIG. 10 is an isometric exploded view of an alternate embodiment of a removable carrier shell and the perforated buttress strip.

FIG. 10 shows an alternate embodiment of a removable carrier shell 191 that can be simultaneously detached from both the anvil 40 and perforated buttress strip 100, releasing the perforated buttress strip 100 from the surgical stapling device 20 in the process. Removable carrier shell 191 and has elongated carrier body 192, hooks 193 with arms 194 and first member 193a extending therefrom and a nose 195. A tang 198 extends from the proximal end of the carrier shell 191, and has a long suture or cable 199 fixedly attached to the tang 116. Perforated buttress strip 100 can be assembled with the removable carrier shell 115 in either manner described previously and shown in FIGS. 8 and 9.

During surgery, removable carrier shell 191 having perforated buttress strip 100 attached thereto are slid onto the anvil 40 of the end effector 35. Cable 199 is then extended proximally from the removable carrier shell 191 along the shaft 30, and terminated with a free end adjacent to the handle 25 of the surgical stapling instrument 20. Placement of the end effector 35 into a patient (through a trocar) leaves the free end of the cable 199 outside of the patient's body. After clamping the end effector 35 on tissue and firing the surgical stapling device 20, the perforated buttress strip 100 is released from the surgical stapling device 20 by pulling on the cable 199. Pulling on the cable 199 simultaneously moves the removable carrier shell 191 distally and detaches it from the anvil 40. As the removable carrier shell 191 moves distally, the arms 194 are withdrawn from the openings 101 within the perforated buttress strip 101 releasing the perforated buttress strip 100 from the removable carrier shell 191 and the anvil 40. Opening the anvil 40 releases the perforated buttress strip 100 and attached tissue from the end effector 35. The cable 199 is then used to withdraw the spent removable carrier shell 115 from the patient through the trocar.

FIG. 11 shows yet another embodiment of removably attaching perforated buttress to a stapling device, a circular stapler 85. In this embodiment, the buttress is released from the circular stapling device by a rotary motion, rather than the linear motion described previously. As shown, the circular stapler 85 has an open circular anvil 89 and a longitudinal axis. An attachment ring 105 is attached to or formed from the circular anvil 89. Tab hooks 106 extend distally from the attachment ring 105 towards the body of the instrument and have tab arms 106a. Tab arms 106a extend from the tab hooks 106 in the same counter clockwise direction around the periphery of the circular anvil 89. The tab hooks 106 are spaced radially outwardly so that the so that circular anvil 85 can fully close without crushing the tab hooks 106.

A perforated buttress ring 107 is provided to attach to the tab hooks 106 extending from the circular anvil 89. A plurality of tabs 108 are spaced about the periphery of the perforated buttress ring 107, with a tab opening 109 extending through each tab 108. As shown, there are four tabs 108 equally spaced about the periphery of the perforated buttress ring 107 and a like number of tab hooks 106. To removably attach the perforated buttress ring 107 to the tab hooks 106 of attachment ring 105, the tab openings 109 are placed onto the tab arms 106a and the perforated buttress ring 107 is rotated clockwise. Likewise, counterclockwise rotation removes an attached perforated buttress ring 107. Alternately, the tab arms 106a can extend in a clockwise direction, in which case the perforated buttress ring 107 is rotated counterclockwise to install and clockwise to remove. After stapling the perforated buttress ring 107 onto tissue, the circular anvil 89 is opened and the circular stapler 85 is rotated clockwise to withdraw the arms 94 from the tab openings and releasing the perforated buttress ring 107 from the circular stapler 85. Since the circular stapler 85 is a single shot instrument, the attachment ring 105 can be permanently or removably attached to the circular anvil 89. Alternately, a perforated buttress ring 107 can be attached over the first circular compression surface 88 by attaching a second attachment ring 105 adjacent to the first circular compression surface 88 with the tab hooks 106 extending distally (not shown). If attachment rings 105 are attached adjacent to both the first and second circular compression surfaces 88,87, care must be taken to orient both sets of attachment ring hooks 94 to prevent contact during closure, and the arms 94 on both attachment rings 105 in the same direction (not shown). With the arms 94 oriented in the same direction, rotating the circular stapler 85 detaches both perforated buttress rings 107 simultaneously.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. An assembly for releasably attaching a buttress material onto a tissue clamping member of a surgical stapling device, said assembly comprising:
    a. a substantially rigid frame for connecting to a top surface of a tissue clamping member of a surgical stapling device when said assembly is disposed thereon; and
    b. a buttress material attached to first and second sides of said frame such that said assembly forms a tubular shape with a hollow lumen extending therethrough, said buttress material for abutting against a bottom surface of a tissue clamping member of a surgical stapling device when said assembly is disposed thereon.

2. The assembly of claim 1 wherein said buttress material has a plurality of openings along first and second sides thereof which engage with hooks along said first and second sides of said frame for attachment of said buttress to said frame.

3. The assembly of claim 1 wherein said frame further includes a rib extending from a bottom surface thereof for engagement with a mating feature on a tissue clamping member.

4. The assembly of claim 1 wherein said frame is made from a substantially rigid plastic.

5. The assembly of claim 1 wherein said buttress material has a substantially continuous surface extending between said first and second sides of said frame.

6. A surgical stapling instrument for clamping and stapling tissue comprising:
    a. a handle, first and a second opposed tissue clamping members connected to said handle and movable between an open position, for receiving tissue therebetween, and a closed position for stapling tissue therebetween, said first clamping member housing a plurality of staples; and
    b. an assembly releasably attached to at least one of said first and second clamping members, said assembly comprising a substantially rigid frame connected to a top surface of said at least one tissue clamping member, and a buttress material attached to first and second sides of said frame, said buttress material abutting against a bottom surface of said at least one tissue clamping member.

7. The instrument of claim 6 wherein said buttress material has a plurality of openings along first and second sides thereof which engage with hooks along said first and second sides of said frame for attachment of said buttress to said frame.

8. The instrument of claim 6 wherein said frame further includes a rib extending from a bottom surface thereof and said at least one clamping member further comprises an indentation for engagement with said rib so as to secure said assembly to said at least one clamping member.

9. The instrument of claim 6 wherein said frame is made from a substantially rigid plastic.

10. The instrument of claim 6 wherein said buttress material substantially covers said bottom surface of said at least one clamping member.

11. A surgical stapling instrument for clamping and stapling tissue comprising:

a. a handle, first and a second opposed tissue clamping members connected to said handle and movable between an open position, for receiving tissue therebetween, and a closed position for stapling tissue therebetween, said first clamping member housing a plurality of staples; and b. an assembly releasably attached to said second clamping member, said assembly comprising a substantially rigid frame connected to a top surface of said second tissue clamping member, and a buttress material attached to first and second sides of said frame such that said assembly forms a tubular shape with a hollow lumen extending therethrough when said assembly is not attached to said at least one clamping member, said buttress material abutting against a bottom surface of said second tissue clamping member.

12. The instrument of claim 11 wherein said buttress material has a plurality of openings along first and second sides thereof which engage with hooks along said first and second sides of said frame for attachment of said buttress to said frame.

13. The instrument of claim 11 wherein said frame further includes a rib extending from a bottom surface thereof and said second clamping member further comprises an indentation for engagement with said rib so as to secure said assembly to said second clamping member.

14. The instrument of claim 11 wherein said frame is made from a substantially rigid plastic.

15. The instrument of claim 11 wherein said buttress material substantially covers said bottom surface of said second clamping member.

* * * * *